(12) United States Patent
Guala

(10) Patent No.: US 6,409,707 B1
(45) Date of Patent: Jun. 25, 2002

(54) ANTI-SIPHON VALVE FOR MEDICAL INFUSION LINES AND THE LIKE

(75) Inventor: Gianni Guala, Turin (IT)

(73) Assignee: Industrie Borla Spa, Moncalieri (IT)

( * ) Notice: Subject to any disclaimer, the term of this patent is extended or adjusted under 35 U.S.C. 154(b) by 99 days.

(21) Appl. No.: 09/635,007

(22) Filed: Aug. 8, 2000

(30) Foreign Application Priority Data

Oct. 22, 1999 (IT) .......................................... TO99A0917

(51) Int. Cl.[7] .............................................. F16K 15/14

(52) U.S. Cl. ...................................... 604/247; 137/843

(58) Field of Search .............................. 604/246, 247; 137/511, 843, 850, 852, 859

(56) References Cited

U.S. PATENT DOCUMENTS

| 3,758,073 | A | * | 9/1973 | Schulte | 604/247 |
|---|---|---|---|---|---|
| 3,807,445 | A | * | 4/1974 | McPhee | 137/843 |
| 3,889,710 | A | * | 6/1975 | Brost | 137/843 |
| 4,244,378 | A | * | 1/1981 | Brignola | 137/843 |
| 4,556,086 | A | * | 12/1985 | Raines | 604/247 |
| 5,465,938 | A | * | 11/1995 | Werge et al. | 137/843 |

* cited by examiner

Primary Examiner—Harry B. Tanner
(74) Attorney, Agent, or Firm—Sughrue Mion, PLLC

(57) ABSTRACT

An anti-siphon valve for medical infusion lines and the like comprises a diaphragm made of elastic material interposed between one first tubular connector and one second tubular connector, and co-operating with an annular valve seat to keep the anti-siphon valve normally closed. The diaphragm consists of the bottom wall of a cup-shaped element, the external peripheral edge of which is normally kept pressed in fluid-tight contact against the annular valve seat under the axial thrust exerted by the side wall of the cup element.

11 Claims, 2 Drawing Sheets

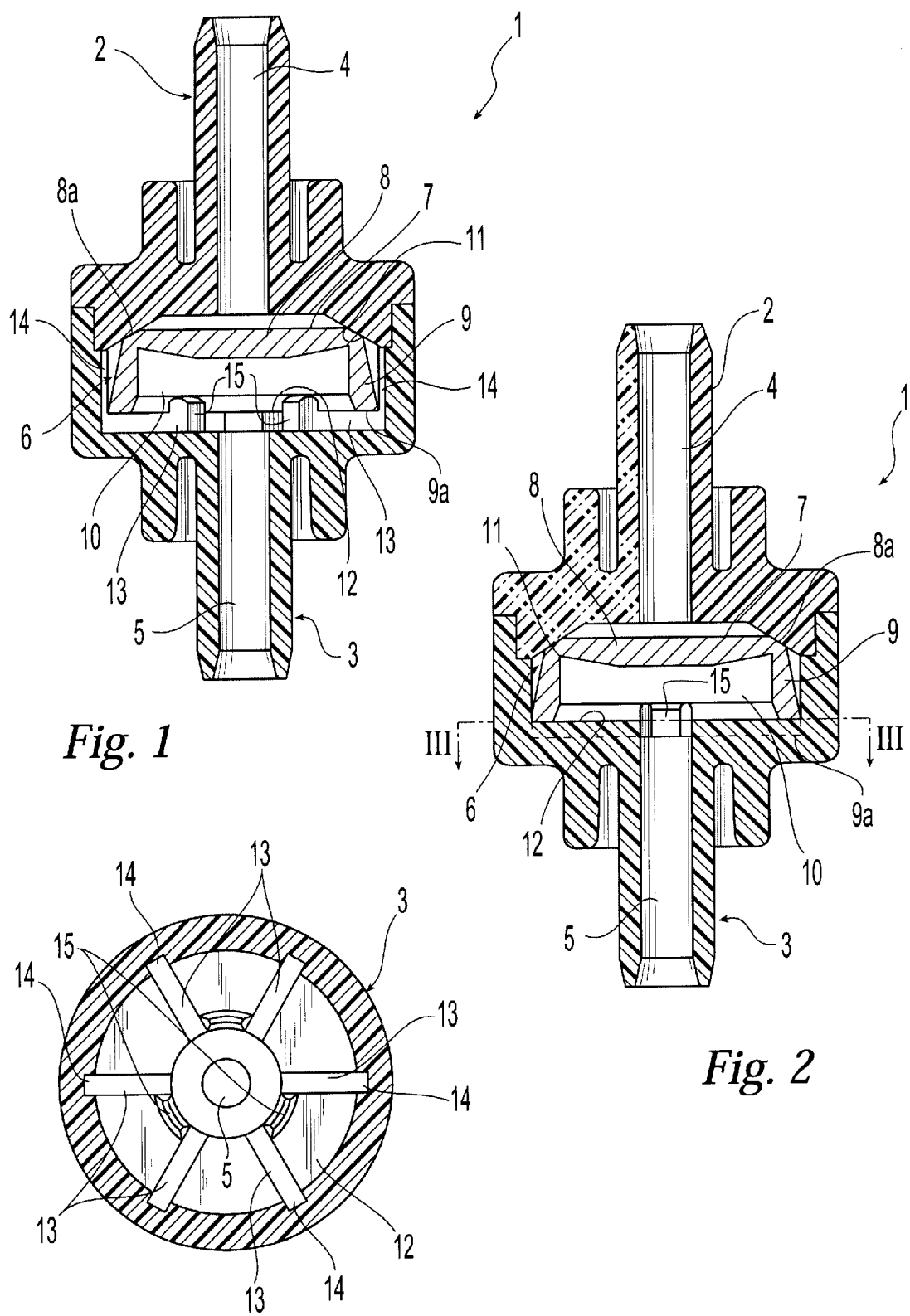

ANTI-SIPHON VALVE FOR MEDICAL INFUSION LINES AND THE LIKE

BACKGROUND OF THE INVENTION

The present invention relates to anti-siphon valves (or non-return valves) for medical infusion lines and the like.

The said valves traditionally comprise a first tubular element and a second tubular element which respectively define a passage upstream and a passage downstream, which are coaxial with one another, and between which is transversely set a diaphragm made of elastically deformable material which cooperates, in a fluid-tight manner, with an annular valve seat of said first tubular element to keep the anti-siphon valve normally closed, and in which a predetermined fluid pressure in said passage upstream causes a deflection of the diaphragm and the consequent opening of the anti-siphon valve.

These valves, which are normally closed, must be able to open promptly when the pressure in the passage upstream is higher than a pre-set threshold value, which is much higher than the one in normal anti-siphon valves used in similar medical applications, and is typically between 1 and 5 psi.

SUMMARY OF THE INVENTION

The primary purpose of the present invention is to provide a valve of the type specified above, which is shaped in such a way as to be able to withstand a relatively high closing preloading, at the same time developing a considerable opening force whenever the fluid pressure in the passage upstream exceeds, albeit by a small amount, the threshold value for which the valve is calibrated.

Another purpose of the present invention is to provide a valve of the aforesaid type, which is shaped so as to meet the above requirement with a simple and inexpensive structure, also in terms of assembly.

A further purpose of the invention is to provide a valve of the aforesaid type that is easy to calibrate, at the moment of fabrication, according to the requirements of use.

According to the invention, the above purpose is achieved essentially thanks to the fact that the said annular valve seat is defined by a conical-surface wall of said first tubular element which diverges towards said second tubular element, and the aforesaid diaphragm consists of the bottom wall of a cup-like element the external peripheral edge of which is normally kept pressed in fluid-tight contact against the annular valve seat under the axial thrust exerted by the side wall of said cup element; the deflection of said bottom wall of the cup element brought about in use by said pre-determined fluid pressure determining the radial contraction of said external peripheral edge and its consequent separation from said annular valve seat.

Thanks to this solution idea, during use, opening of the valve takes place promptly even if the diaphragm consisting of the bottom wall of the cup-like element is subjected to a high axial preloading which ensures maximum safety and reliability of closing of the valve. In fact, the thrust exerted by the pressure upon reaching of the threshold value against the bottom wall of the cup-like element produces an elastic deformation of the latter into a concave conformation which is substantially hemispherical, and as a result of which the peripheral edge of said bottom wall separates from the conical-surface valve seat with an effect which is, so to speak, amplified. In practice, a modest pressure value beyond the above-mentioned threshold value is therefore sufficient to cause opening of the valve according to the invention in a prompt and immediate way.

In the valve-open condition, as the flow rate of the fluid increases there is a proportionally greater deformation of the bottom wall of the cup-like element and, consequently, a proportionally greater removal of its peripheral edge from the valve seat. In this way, the head loss through the valve follows a linear pattern.

In addition, in the valve-open condition, the thrust exerted by the fluid against the external surface of the area of the side wall of the cup element which is adjacent to the bottom wall contributes to keeping the valve open.

According to a preferred embodiment of the invention, the free edge of the side wall of said cup element conveniently rests against a grooved surface of said second tubular element communicating with said passage downstream, and the side wall of the cup element conveniently has a conical surface diverging towards said grooved surface of the second tubular element.

Alternatively, said surface may be cylindrical.

BRIEF DESCRIPTION OF THE DRAWINGS

The invention will now be described in detail with reference to the attached drawings, which are provided purely as non-limiting examples and in which:

FIG. 1 is a schematic axial section illustrating an axial connector for medical infusion lines, incorporating an anti-siphon valve according to the invention;

FIG. 2 is a section similar to FIG. 1 but rotated through 90°;

FIG. 3 is a cross-sectional view taken along the line III—III of FIG. 2;

DETAILED DESCRIPTION OF THE INVENTION

Figure 4:
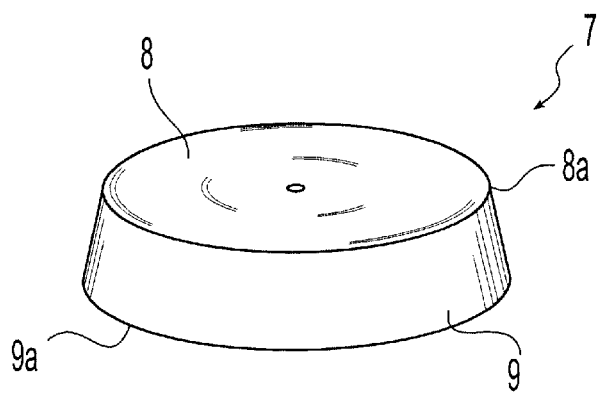
FIG. 4 is a perspective view of the open-close element of the valve according to the invention.

With reference first to FIGS. 1–3, number 1 designates as a whole an axial connector for tube-to-tube connection for medical infusion lines, transfusion lines, and the like. It should be noted immediately that the connector could also be arranged for luer-tube or tube-tube or luer-luer connection.

The connector 1 comprises, in a way that is in itself generally known, a first tubular connector 2 and a second tubular connector 3 which are both normally made of an appropriate moulded thermoplastic material such as polycarbonate, and which are joined together coaxially in a permanent way, for example by means of ultrasound welding, or gluing, or using equivalent means.

The first tubular connector 2 and second tubular connector 3 respectively define a passage upstream or inlet passage 4 and a passage downstream or outlet passage 5, which can be connected to respective sections of tubing of an infusion medical line or the like.

Between the passage upstream 4 and the passage downstream 5 an anti-siphon valve generically designated by 6 is arranged, which specifically forms the subject of the present invention.

The anti-siphon valve 6 basically comprises an elastic open-close element consisting of a cup-like element 7, illustrated in detail in FIG. 4 in its undeformed resting condition. This cup element 7 comprises a circular bottom wall 8 and a skirt or side wall 9 having a cylindrical shape, or more conveniently a conical surface diverging on the side opposite to the bottom wall 8.

The bottom wall 8 may have a constant thickness or, more conveniently, a variable thickness that increases towards the central part of the wall, as illustrated.

Likewise, the side wall 9 may have a constant thickness, or else, more conveniently, a variable thickness that increases towards the free edge 9a of the wall (i.e., the edge opposite to the bottom wall 8), as illustrated.

The external circumferential edge of the bottom wall 8, designated by 8a, may be a sharp edge, as in the case of the example illustrated, or may be chamfered.

The cup element 8 is normally made out of a single piece of soft elastomeric material, in particular injection-moulded liquid silicone with a central injection point.

Referring back to FIGS. 1–3, the cup element 7 is inserted in a chamber 10 defined between the first tubular element 2 and the second tubular element 3 and coaxial with these elements. The chamber 10 is delimited on one side by an annular wall 11 of the first tubular element 2, which preferably presents a conical surface diverging towards the second tubular element 3 and defines an annular valve seat. On the opposite side, the chamber 10 is delimited by a grooved surface 12 which is coaxial to the outlet passage 5 and is made up of a series of radial channels 13 arranged like spokes and communicating with said outlet passage 5.

The radially external end of each radial channel 13 is prolonged with a respective axial channel 14 formed in the wall of the second tubular element 3 which delimits the chamber 10 laterally. In addition, formed on the grooved surface 12, around the outlet passage 5, are axial projections 15, the function of which will be clarified in what follows.

The cup element 7 is housed coaxially within the chamber 10, with its bottom wall 8 facing, like a transverse diaphragm, the inlet passage 4, and with its side wall 9 facing the axial channels 14. The free edge 9a of the side wall 9 rests on the grooved surface 12 of the second tubular element 3.

The external circumferential edge 8a of the bottom wall 8 rests against the annular valve seat defined by the conical surface 11 of the first tubular element 2. The arrangement is such that, in the mounted condition illustrated in FIGS. 1 and 2, the cup element 7 is subjected to a pre-determined axial elastic preloading. In this way, the peripheral edge 8a of the bottom wall 8 is elastically kept pressed in sealed contact against the annular seat valve 11, under the axial thrust exerted by the side wall 9, as well as under the resulting radial thrust exerted by the wall 8 of the cup element 7 thanks to the conical conformation of the valve seat 11. This condition corresponds to the normally closed position of the anti-siphon valve 6 according to the invention, in which flow from the passage upstream 4 to the passage downstream 5 is prevented in an effective and safe way.

Figure 5:
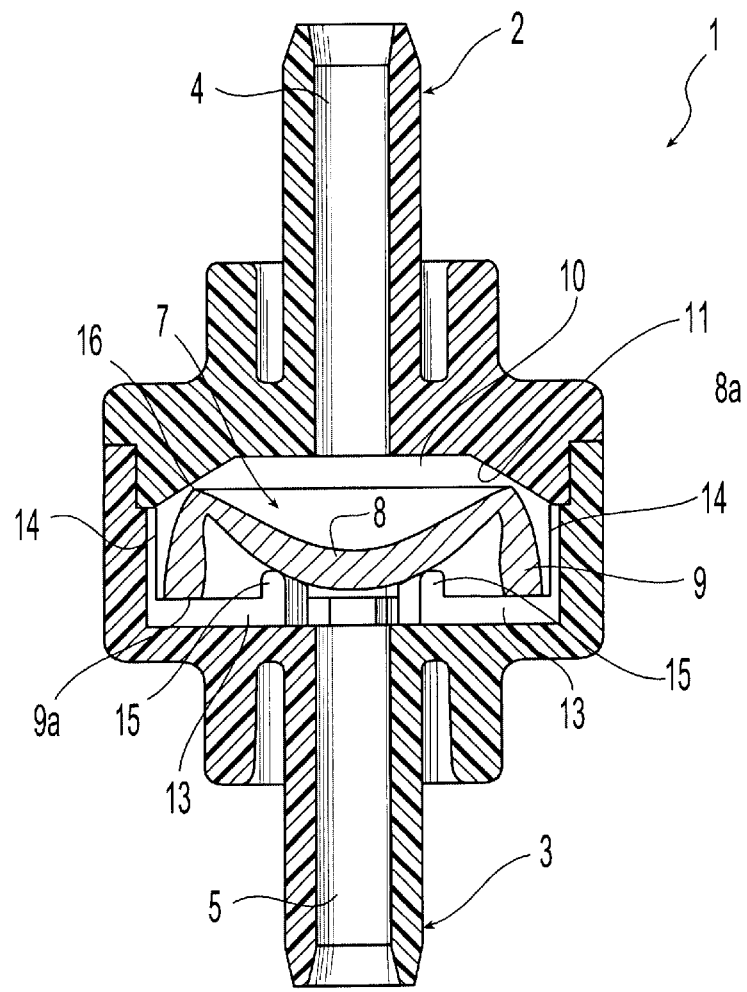
FIG. 5 is a view similar to FIG. 1 which illustrates the valve in the open position.

Whenever inside the passage upstream 2 an overpressure is produced that exceeds a pre-set threshold value, for example of the order of 1–5 psi, the anti-siphon valve 6 promptly switches from the closed condition to the open condition illustrated in FIG. 5, as a result of the deflection of the bottom wall 8 of the cup element 7, possibly combined with partial axial elastic yielding of the side wall 9. This deflection causes the peripheral edge 8a of the cup element 7 to move away from the annular valve seat 11, and this generates an annular port 16. The passage upstream 4 is thus set into communication with the passage downstream 5 through said annular port 16, the axial channels 14 facing the side wall 9 of the cup element 7, and the radial channels 13 situated underneath the free edge 9a of the side wall 9.

As has already been mentioned previously, opening of the valve 6 occurs promptly even if the diaphragm consisting of the bottom wall 8 of the cup element 7 is subjected to a high axial preloading that ensures its maximum safety and reliability in closing. In fact, the thrust exerted by the pressure upon reaching of the threshold value against the bottom wall 8 causes elastic deformation of the latter in a substantially hemispherical concave conformation, as a result of which the peripheral edge 8a separates from the conical-surface valve seat with a certain degree of amplification. In practice, then, a modest pressure value beyond the threshold value is sufficient for causing, in a prompt and immediate way, the valve 6 to open, at the same time also reducing any risk of undesired adhesion between the edge 8a and the valve seat 11, also following upon prolonged periods of closing of the valve which could jeopardise opening of the latter.

In the valve-open condition, as the flow rate of the fluid increases, there is a proportionally greater deformation of the bottom wall 8 of the cup element 7 and, consequently, a proportionally greater widening of the port 16. The head loss through the valve 6 is therefore approximately linear.

The axial projections 15 on the grooved surface 12 have the function of preventing the bottom wall 8 thus deformed from obstructing the outlet passage 5.

In the valve-open condition, the thrust exerted by the fluid against the external surface of the area of the side wall 9 of the cup element 7 that is adjacent to the bottom wall 8 of the same element 7 contributes to keeping the valve open.

Return to the closed position of the anti-siphon valve 6, when the balance of pressure is restored between the passage upstream 4 and the passage downstream 5, or else in the case of overpressure in the passage downstream 5, comes about immediately as a result of the return of the bottom wall 8 to the non-deflected configuration where it rests its peripheral edge 8a against the annular valve seat 11.

Calibration of the anti-siphon valve 1 described above is simply by operating on the elastic characteristics of the cup element 7, for example by varying the thickness of its bottom wall 8 or by using materials with a different hardness, or else by modifying the assembly preloading within the chamber 10, or again by varying the conicity of the valve seat 11. This makes it possible to adapt the valve also for use as a simple check valve pre-set for opening with considerably more modest fluid pressures, of the order of 0.01–0.2 bar.

Of course, without prejudice to the principle of the invention, the details of construction and the embodiments may vary widely with respect to what is herein described and illustrated purely for the purpose of providing an example, without thereby departing from the sphere of the present invention as defined in the appended claims.

What is claimed is:

1. An anti-siphon valve for medical infusion lines and the like, comprising one first tubular connector and one second tubular connector which define, respectively, a passage upstream and a passage downstream which are coaxial to one another, and a diaphragm arranged transversely between said first and second tubular connectors, said diaphragm being made of elastically deformable material and co-operating in a fluid-tight manner with an annular valve seat of said first tubular element to keep said anti-siphon valve normally closed, in which a pre-determined pressure of the fluid in said passage upstream causes a deflection of said diaphragm and opening of said anti-siphon valve, wherein said annular valve seat is defined by a conical-surface wall of said first tubular element, which diverges towards said second tubular element, and wherein said diaphragm consists of the bottom wall of a cup-shaped element having a side wall, said bottom wall having an external peripheral edge which is normally kept pressed in fluid-tight contact against said annular valve seat under the axial thrust exerted by said side wall of said cup element; the deflection of said bottom wall of said cup element produced in use by said pre-determined fluid pressure causing radial contraction of said external peripheral edge and consequent separation thereof from said annular valve seat.

2. A valve according to claim 1, wherein said side wall of the said cup element has a free edge resting against a grooved surface of said second tubular element communicating with said passage downstream.

3. A valve according to claim 1, wherein said side wall of said cup element has a cylindrical surface.

4. A valve according to claim 2, wherein said side wall of said cup element has a conical surface diverging towards said grooved surface.

5. A valve according to claim 2, wherein said grooved surface has series of radial channels arranged like spokes, each of which is prolonged in a respective axial channel formed in said second tubular element alongside said side wall of said cup element.

6. A valve according to claim 5, wherein said grooved surface has axial projections set around said outlet passage.

7. A valve according to claim 1, wherein said bottom wall of said cup element has a variable thickness, increasing towards its central part.

8. A valve according to claim 1, wherein said side wall of said cup element has a variable thickness, increasing towards a free edge thereof.

9. A valve according to claim 1, wherein said external peripheral edge of the bottom wall of said cup element is a sharp edge.

10. A valve according to claim 1, wherein said cup element is formed in a single piece of soft elastomeric material, namely injection-moulded liquid silicone with a central injection point.

11. A valve according to claim 1, wherein said first tubular element and second tubular element are arranged for tube-tube connection, or luer-tube connection, or tube-luer connection, or luer-luer connection of said medical line.

* * * * *